United States Patent [19]

Toki et al.

[11] Patent Number: 5,304,657
[45] Date of Patent: Apr. 19, 1994

[54] HYDRAZINE COMPOUNDS USESFUL AS PESTICIDES

[75] Inventors: Tadaaki Toki; Toru Koyanagi; Kiyomitsu Yoshida; Kazuhiro Yamamoto; Masayuki Morita, all of Kusatsu, Japan

[73] Assignee: Ishihara Sangyo Kaisha Ltd., Osaka, Japan

[21] Appl. No.: 774,786

[22] Filed: Oct. 10, 1991

[30] Foreign Application Priority Data

Oct. 29, 1990 [JP] Japan .................. 2-291107

[51] Int. Cl.$^5$ .................. C07D 333/68; C07D 333/70
[52] U.S. Cl. .................. 549/57; 546/169; 549/50; 549/51; 549/54; 549/55; 549/436; 564/149
[58] Field of Search .................. 549/50, 54, 55, 51, 549/57, 437, 438, 439, 440, 443, 444; 71/90; 514/443; 504/289, 298

[56] References Cited

U.S. PATENT DOCUMENTS

| | | | |
|---|---|---|---|
| 4,857,550 | 8/1989 | Kameswaran et al. | 514/552 |
| 4,985,461 | 1/1991 | Hsu et al. | 514/615 |
| 5,117,057 | 5/1992 | Hsu et al. | 558/6 |

FOREIGN PATENT DOCUMENTS

| | | |
|---|---|---|
| 0228564 | 7/1987 | European Pat. Off. . |
| 0232075 | 8/1987 | European Pat. Off. . |
| 0234944 | 9/1987 | European Pat. Off. . |
| 0245950 | 11/1987 | European Pat. Off. . |
| 0253468 | 1/1988 | European Pat. Off. . |
| 0261755 | 3/1988 | European Pat. Off. . |
| 0286746 | 10/1988 | European Pat. Off. . |
| 0347216 | 12/1989 | European Pat. Off. . |
| 0361645 | 4/1990 | European Pat. Off. . |
| 0395581 | 10/1990 | European Pat. Off. . |
| 0398842 | 11/1990 | European Pat. Off. . |
| 2-207066 | 8/1990 | Japan . |
| 3-141245 | 6/1991 | Japan . |
| 3-145447 | 6/1991 | Japan . |

*Primary Examiner*—Richard L. Raymond
*Attorney, Agent, or Firm*—Oblon, Spivak, McClelland, Maier & Neustadt

[57] ABSTRACT

A hydrazine compound of the formula (I) or its salt:

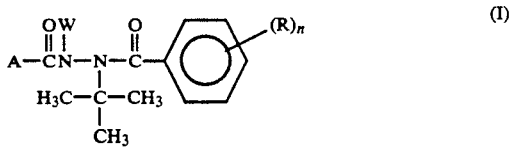

wherein A is a benzofuranyl group which may be substituted, a quinolinyl group which may be substituted, a benzothienyl group which may be substituted, a benzothiazolyl group which may be substituted, a thienothienyl group which may be substituted, a dihydrothienothienyl group which may be substituted, a dihydrocyclopentathienyl group which may substituted, a tetrahydrobenzothienyl group which may be substituted, an indanyl group which may be substituted, or a hexahydroindanyl group which may be substituted, W is a hydrogen atom, a cyano group, —COCOOR', —S—N(R")COOR' or —CH$_2$OCOR', wherein each of R' and R" which are independent from each other, is an alkyl group or a cycloalkyl group, R is a halogen atom, an alkyl group which may be substituted by a halogen atom, an alkoxy group which may substituted by a halogen atom, an alkylthio group which may be substituted by a halogen atom, or a nitro group, n is an integer of from 0 to 5, provided that when n is 2 or more, the plurality of R may be the same or different.

6 Claims, No Drawings

HYDRAZINE COMPOUNDS USESFUL AS PESTICIDES

The present invention relates to novel hydrazine compounds or their salts, processes for producing them and pesticides containing them.

It is disclosed, for example, in U.S. Pat. No. 4,985,461, EP 232075A, EP 245950A, EP 234944A, EP 253468A, EP 261755A, EP 286746A, EP 228564A, EP 347216A, U.S. Pat. No. 4,857,550, Japanese Unexamined Patent Publication No. 207066/1990, EP 395581A, EP 398842A, Japanese Unexamined Patent Publication No. 141245/1991 and Japanese Unexamined Patent Publication No. 145447/1991 that hydrazine compounds having a structure of the formula:

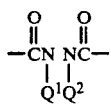

wherein $Q^1$ is a hydrogen atom, —CN, —COCOOR', —S—N(R")COOR' or the like, wherein each of R' and R" which are independent from each other, is an alkyl group, and $Q^2$ is a tert-butyl group or a substituted alkyl group, have insecticidal activities.

However, these prior art references do not disclose compounds of the formula (I) given below having substituent A as defined below, like the compounds of the present invention.

The present invention provides hydrazine compounds of the following formula (I) or their salts, processes for producing them and pesticidal compositions containing them:

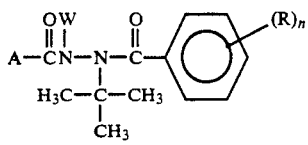

wherein A is a benzofuranyl group which may be substituted, a quinolinyl group which may be substituted, a benzothienyl group which may be substituted, a benzothiazolyl group which may be substituted, a thienothienyl group which may be substituted, a dihydrothienothienyl group which may be substituted, a dihydrocyclopentathienyl group which substituted, a tetrahydrobenzothienyl group which may be substituted, an indanyl group which may be substituted, or a hexahydroindanyl group which may be substituted, W is a hydrogen atom, a cyano group, —COCOOR', —S—N(R")COOR' or —CH$_2$OCOR', wherein each of R' and R" which are independent from each other, is an alkyl group or a cycloalkyl group, R is a halogen atom, an alkyl group which may be substituted by a halogen atom, an alkoxy group which may substituted by a halogen atom, an alkylthio group which may be substituted by a halogen atom, or a nitro group, n is an integer of from 0 to 5, provided that when n is 2 or more, the plurality of R may be the same or different.

Now, the present invention will be described in detail with reference to the preferred embodiments.

In the above formula (I), A includes a benzofuranyl group which may be substituted, a quinolinyl group which may be substituted, a benzothienyl group which may be substituted, a benzothiazolyl group which may be substituted, a thienothienyl group which may be substituted, a dihydrothienothienyl group which may be substituted, a dihydrocyclopentathienyl group which may be substituted, a tetrahydrobenzothienyl group which may be substituted, an indanyl group which may be substituted and a hexahydroindanyl group which may be substituted, and the substituents of these groups include, for example, a halogen atom, an alkyl group which may be substituted by a halogen atom, an alkoxy group which may be substituted by a halogen atom, and an alkylthio group which may be substituted by a halogen atom, or a nitro group. The number of substituents may be one or more. The halogen atom for each of A and R may, for example, be a fluorine atom, a chlorine atom, a bromine atom or an iodine atom, and the alkyl group or the alkyl moiety for each of A, R, R' and R" may be the one having from 1 to 6 carbon atoms, such as a methyl group, an ethyl group, a propyl group, a butyl group, a pentyl group or a hexyl group, and it may have a straight chain structure or a branched aliphatic chain structure such as an isopropyl group or a tert-butyl group. The cycloalkyl group for each of R' and R" may, for example, be the one having from 3 to 6 carbon atoms, such as a cyclopropyl group, a cyclobutyl group, a cyclopentyl group or a cyclohexyl group.

When the number of substituents is 2 or more in the benzofuranyl group which may be substituted, the quinolinyl group which may be substituted, the benzothienyl group which may be substituted, the benzothiazolyl group which may be substituted, the thienothienyl group which may be substituted, the dihydrothienothienyl group which may be substituted, the dihydrocyclopentathienyl group which may be substituted, the tetrahydrobenzothienyl group which may be substituted, the indanyl group which may be substituted, or the hexahyroindanyl group which may be substituted, for A in the formula (I), the plurality of substituents for each group may be the same or different. Further, when n in $(R)_n$ is 2 or more, the plurality of R may be the same or different.

The salt of the compound of the formula (I), wherein W is a hydrogen atom, may be a salt with a basic substance, such as an ammonium salt, an alkali metal salt or an alkaline earth metal salt. The alkali metal salt includes, for example, a sodium salt, a potassium salt and a lithium salt. The alkaline earth metal salt includes, for example, a calcium salt, a magnesium salt and a barium salt.

Among the compounds of the formula (I), preferred are those wherein A is a benzothienyl group which may be substituted, a thienothienyl group which may be substituted, a dihydrocyclopentathienyl group which may be substituted, or a tetrahydrobenzothienyl group which may be substituted, W is a hydrogen atom, R is a halogen atom or an alkyl group, and n is 1 or 2. Among these preferred compounds, more preferred are those wherein A is a substituted benzothienyl group, a dihydrocyclopentathienyl group which may be substituted, or a tetrahydrobenzothienyl group which may be substituted. Among these more preferred compounds, most preferred are N'-t-butyl-N'-3,5-dimethylbenzoyl-N-benzo[b]thiophene-2-carbohydrazide (Compound No. 5 as described hereinafter), N'-t-butyl-N'-3,5-dimethylbenzoyl-N-5,6-dihydro-4H-cyclopenta[b]thiophene-2-carbohydrazide (Compound No. 34 as described hereinafter) and N'-t-butyl-N'-3,5-dimethylbenzoyl-N-4,5,6,7- tetrahydrobenzo[b]thiophene-2-carbohydrazide (Compound No. 35 as described hereinafter).

Among the compounds of the formula (I), those wherein W is a hydrogen atom, can be prepared, for example, by a process of the following reaction step a:

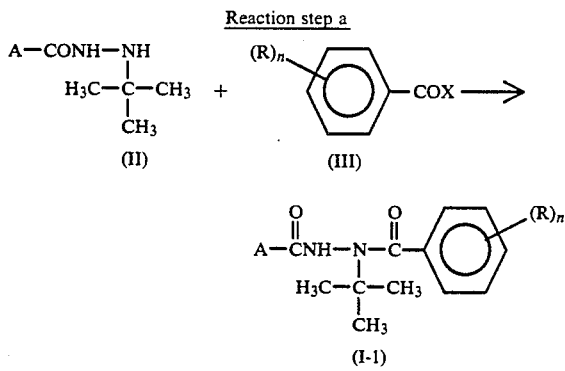

In the above formulas, A, R and n are as defined above, and X is a halogen atom, an alkoxy group or —OCOT wherein T is an alkyl group.

The reaction step a is conducted usually in the presence of a solvent and a base. As the solvent, a solvent inert to the reaction, such as, water; an aromatic hydrocarbon such as benzene or toluene; an ether such as diethyl-ether or tetrahydrofuran; a halogenated hydrocarbon such as methylene chloride or chloroform; or an aprotic polar solvent such as acetonitrile, dimethylformamide or pyridine, may be mentioned. These solvents may be used alone or in combination as a mixture. Particularly preferred is a solvent mixture of water and toluene or a solvent mixture of water and methylene chloride. As the base, a tertiary amine such as triethylamine; an alkali metal hydroxide such as sodium hydroxide or potassium hydroxide; an alkali metal carbonate such as sodium carbonate or potassium carbonate; an alkoxide such as sodium methoxide or sodium ethoxide; or pyridine, may be mentioned. Particularly preferred is sodium hydrosxide. Pyridine being a base which can be used also as a solvent, is also preferred. The reaction temperature is usually from $-50°$ C. to $+100°$ C., preferably from $0°$ C. to $30°$ C. in a case where X in the compound of the formula (III) is a halogen atom or —OCOT, or from $50°$ C. to $100°$ C. in a case where X is an alkoxy group. The reaction time is usually from 0.1 to 24 hours, preferably from 0.5 to 3 hours.

The compound of the formula (II) can be prepared, for example, by a process of the following reaction step b.

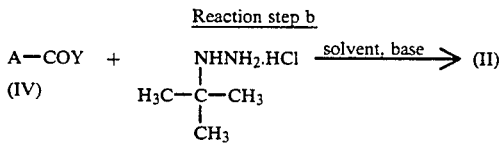

In the formula (IV), A is as defined above, and Y is a halogen atom or an alkoxy group.

As the solvent which can be used for the reaction step b, an alcohol such as methanol or ethanol may be mentioned in addition to the solvents which can be used for the above reaction step a. These solvents may be used alone or in combination as a mixture. Particularly preferred is methanol or a solvent mixture of water and toluene. As the base which can be used for the reaction step b, the same bases as those useful for the above reaction step a, may be mentioned. Among them, sodium hydroxide or sodium methoxide is preferred. The reaction temperature for the reaction step b is usually from $-20°$ C. to $+100°$ C., preferably from $0°$ C. to $50°$ C. in a case where Y in the compound of the above formula (IV) is a halogen atom, or from $80°$ C. to $100°$ C. in a case where Y is an alkoxy group. The reaction time is usually from 0.1 to 24 hours, preferably from 0.5 to 5 hours.

The compound of the above formula (IV) can be prepared by the following reaction steps c to d using a starting material of the after-mentioned formula (V) which can be prepared by a process disclosed in e.g. J. Org. Chem. vol. 21,39–44 (1956), and J. Chem. Soc. C, 1225–1227 (1968).

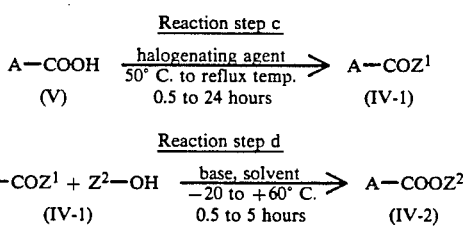

In the above formulas, A is as defined above, $Z^1$ is a halogen atom, and $Z^2$ is an alkyl group.

In the reaction step c, the halogenating agent may, for example, be thionyl chloride, phosphorus oxychloride or thionyl bromide. In the reaction step d, the base may, for example, be a tertiary amine such as triethylamine; or pyridine, and the solvent may, for example, be other than water among the solvents useful for the above reaction step a.

Now, the specific Synthesis Examples of the compounds of the present invention wherein W is a hydrogen atom, will be described.

SYNTHESIS EXAMPLE 1

Synthesis of
N'-t-butyl-N'-3,5-dimetylbenzoyl-N-benzo[b]thiophene-2-carbohydrazide (Compound No. 5 as described hereinafter)

(1) 1.0 g of benzo[b]thiophene-2-carboxylic acid was reacted with 2 ml of thionyl chloride under reflux overnight, and then excess thionyl chloride was distilled off under reduced pressure to obtain benzo[b]thiophene-2-carbonyl chloride as a solid product.

2.2 g of a 28% sodium methoxide methanol solution was dropwise added under cooling with ice to a solution having 1.4 g of N-t-butylhydrazine hydrochloride dissolved in 15 ml of methanol, and the mixture was stirred at the same temperature for 15 minutes. Then, 2 ml of a methylene chloride solution of the above benzo[b]thiophene-2-carbonyl chloride was gradually added thereto. The mixture was reacted at the same temperature for one hour under stirring, and the reaction mixture was put into water and extracted with ethyl acetate. Then, the organic layer was washed with water and dried over anhydrous sodium sulfate. Then, the solvent was distilled off under reduced pressure, and a crude product thereby obtained was purified by silica gel column chromatography (eluting solution: methylnene chloride/ethyl acetate=2/1) to obtain 1.1 g of N'-t-butyl-N-benzo[b]thiophene-2-carbohydrazide (Intermediate No. 5 as described hereinafter) having a melting point of from 147° to 148° C.

(2) 220 mg of 3,5-dimethylbenzoyl chloride was dropwise added under cooling with ice to a solution having 300 mg of N'-t-butyl-N-benzo[b]thiophene-2-carbohydrazide obtained in the above step (1) dissolved in 3 ml of pyridine. The mixture was reacted at the same temperature for one hour under stirring. Then, the reaction mixture was put into water and extracted with ethyl acetate. Then, the organic layer was washed with water and dried over anhydrous sodium sulfate. Then, the solvent was distilled off under reduced pressure, and a crude product thereby obtained was purified by silica gel column chromatography (eluting solution: methylene chloride/ethyl acetate=95/5) to obtain 400 mg of the desired product (Compound No. 5 as described hereinafter) having a melting point of from 211° to 213° C.

SYNTHESIS EXAMPLE 2

Synthesis of N'-t-butyl-N'-3,5-dimethylbenzoyl-N-6-fluorobenzo[b]-thiophene-2-carbohydrazide (Compound No. 22 as described hereinafter)

(1) 10 g of 4-fluorobenzaldehyde was dropwise added at room temperature to a solution having 10.8 g of rhodanine and 20 g of sodium acetate suspended in 100 ml of acetic acid. The obtained mixture was reacted under reflux for two hours and then cooled to room temperature. Then, this reaction mixture was put into about 500 ml of water, and a solid product thereby obtained was collected by filtration, washed with water and dried to obtain 16.4 g of 5-(4-fluorobenzylidene)rhodanine.

(2) 8.3 g of sodium hydroxide was dissolved in 700 ml of water, and the solution was heated to about 70° C. Then, 10 g of 5-(4-fluorobenzylidene)rhodanine obtained in the above step (1) was put into the solution, and the mixture was reacted at the same temperature for 20 minutes. After completion of the reaction, the reaction solution was cooled to a temperature of at most 10° C. and 20 ml of concentrated hydrochloric acid was dropwise added thereto. A solid product thereby obtained was collected by filtration, washed with water and dried to obtain 6.1 g of 3-(4-fluorophenyl)-2-mercaptoacrylic acid.

(3) A mixture of 12 g of iodine and 80 ml of nitrobenzene was heated to about 190° C. to obtain a solution. Then, 1.5 g of 3-(4-fluorophenyl)-2-mercaptoacrylic acid obtained in the above step (2) was put into the solution, and the mixture was reacted for two minutes under stirring. After completion of the reaction, the reaction solution was cooled to room temperature and extracted with 100 ml of a 1% sodium hydroxide aqueous solution. A proper amount of sodium hydrogensulfite was added to the extract, and then concentrated hydrochloric acid was dropwise added to bring the pH to 1. The precipitate was collected by filtration, washed with water and then with hexane and dried to obtain 910 mg of 6-fluorobenzo[b]thiophene-2-carboxylic acid.

(4) 700 mg of 6-flurorobenzo[b]thiophene-2-carboxylic acid obtained in the above step (3) was reacted with 2 ml of thionyl chloride under reflux overnight. Then, excess thionyl chloride was distilled off under reduced pressure to obtain 6-fluorobenzo[b]thiophene-2-carbonyl chloride.

1.4 g of a 28% sodium methoxide methanol solution was dropwise added under cooling with ice to a solution having 900 mg of N-t-butylhydrazine hydrochloride dissolved in 9 ml of methanol, and the mixture was stirred at the same temperature for 15 minutes. Then, 2 ml of a methylene chloride solution of the above 6-fluorobenzo[b]thiophene-2-carbonyl chloride was gradually added thereto. The mixture was reacted at the same temperature for one hour under stirring. Then, the reaction mixture was put into water and extracted with ethyl acetate. Then, the organic layer was washed with water and dried over anhydrous sodium sulfate. Then, the solvent was distilled off under reduced pressure, and a crude product thereby obtained was purified by silica gel column chromatography (eluting solution: methylene chloride/ethyl acetate=2/1) to obtain 720 mg of N'-t-butyl-N-6-fluorobenzo[b]thiophene-2-carbohydrazide (Intermediate No. 16 as described hereinafter) having a melting point of 175° to 176° C.

(5) 0.5 ml of a methylene chloride solution containing 210 mg of 3,5-dimethylbenzoyl chloride was dropwise added under cooling with ice to a solution having 300 mg of N'-t-butyl-N-6-fluorobenzo[b]thiophene-2-carbohydrazide obtained in the above step (4) dissolved in 3 ml of pyridine. The mixture was reacted at the same temperature for one hour under stirring. Then, the reaction mixture was put into water and extracted with ethyl acetate. Then, the organic layer was washed with water and dried over anhydrous sodium sulfate. Then, the solvent was distilled off under reduced pressure, and a crude product thereby obtained was purified by silica gel column chromatography (eluting solution: methylene chloride/ethyl acetate=95/5) to obtain 420 mg of the desired product (Compound No. 22 as described hereinafter) having a melting point of 243° to 244° C.

SYNTHESIS EXAMPLE 3

Synthesis of N'-t-butyl-N'-3,5-dimethylbenzoyl-N-5,6-dihydro-4H-cyclopenta[b]thiophene-2-carbohydrazide (Compound No. 34 as described hereinafter)

(1) 1.0 g of 5,6-dihydro-4H-cyclopenta[b]thiophene-2-carboxylic acid was reacted with 4 ml of thionyl chloride for 3.5 hours under reflux. Then, excess thionyl chloride was distilled off under reduced pressure to obtain 5,6-dihydro-4H-cyclopenta[b]thiophene-2-carbonyl chloride.

2.41 g of a 28% sodium methoxide methanol solution was dropwise added under cooling with ice to a solution having 1.48 g of N-t-butylhydrazine hydrochloride dissolved in 17 ml of methanol. The mixture was stirred at the same temperature for 30 minutes. Then, a solution having the above 5,6-dihydro-4H-cyclopenta[b]thiophene-2-carbonyl chloride dissolved in 7 ml of methylene chloride, was gradually added thereto. The mixture was reacted at the same temperature for one hour under stirring. Then, the reaction mixture was put into water and extracted with ethyl acetate. Then, the organic layer was washed with water and dried over anhydrous sodium sulfate. Then, the solvent was distilled off under reduced pressure, and a crude product thereby obtained was purified by silica gel column chromatography (eluting solution: methylene chloride/ethyl acetate=3/1) to obtain 0.86 g of N'-t-butyl-N-5,6-dihydro-4H-cyclopenta[b]thiophene-2-carbohydrazide (Intermediate No. 28 as described hereinafter) having a melting point of from 163° to 164° C.

(2) A solution having 544 mg of 3,5-dimethylbenzoyl chloride dissolved in 2 ml of methylene chloride, was dropwise added under cooling with ice to a solution having 700 mg of N'-t-butyl-N-5,6-dihydro-4H-cyclopenta[b]thiophene-2-carbohydrazide obtained in the above step (1) dissolved in 9 ml of pyridine. The mixture was reacted at the same temperature for 1.5 hours. Then, the reaction mixture was put into water and extracted with ethyl acetate. Then, the organic layer was washed with water and dried over anhydrous sodium sulfate. Then, the solvent was distilled off under reduced pressure, and a crude product thereby obtained was purified by silica gel column chromatography (eluting solution: methylene chloride/ethyl acetate=95/5) to obtain 0.88 g of the desired product (Compound No. 34 as described hereinafter) having a melting point of from 231° to 232° C.

SYNTHESIS EXAMPLE 4

Synthesis of N'-t-butyl-N'-3,5-dimethylbenzoyl-N-4,5,6,7-tetrahydrobenzo[b]thiophene-2-carbohydrazide (Compound No. 35 as described hereinafter)

(1) 1.0 g of 4,5,6,7-tetrahydrobenzo[b]thiophene-2-carboxylic acid was reacted with 4 ml of thionyl chloride for 3.5 hours under reflux. Then, excess thionyl chloride was distilled off under reduced pressure to obtain 4,5,6,7-tetrahydrobenzo[b]thiophene-2-carbonyl chloride.

2.22 g of a 28% sodium methoxide methanol solution was dropwise added under cooling with ice to a solution having 1.37 g of N-t-butylhydrazine hydrochloride dissolved in 16 ml of methanol. The mixture was stirred at the same temperature for 30 minutes. Then, a solution having the above 4,5,6,7-tetrahydrobenzo[b]thiophene-2-carbonyl chloride dissolved in 7 ml of methylene chloride, was gradually added thereto. The mixture was reacted at the same temperature for one hour under stirring. Then, the reaction mixture was put into water and extracted with ethyl acetate. Then, the organic layer was washed with water and dried over anhydrous sodium sulfate. Then, the solvent was distilled off under reduced pressure, and a crude product thereby obtained was purified by silica gel column chromatography (eluting solution: methylene chloride/ethyl acetate=3/2) to obtain 0.72 g of N'-t-butyl-N-4,5,6,7-tetrahydrobenzo[b]thiophene-2-carbohydrazide (Intermediate No. 29 as described hereinafter) having a melting point of from 155° to 157° C.

(2) A solution having 512 mg of 3,5-dimethylbenzoyl chloride dissolved in 2 ml of methylene chloride, was dropwise added under cooling with ice to a solution having 700 mg of N'-t-butyl-N-4,5,6,7-tetrahydrobenzo[b]thiophene-2-carbohydrazide obtained in the above step (1) dissolved in 8 ml of pyridine. The mixture was reacted at the same temperature for 1.5 hours. Then, the reaction mixture was put into water and extracted with ethyl acetate. Then, the organic layer was washed with water and dried over anhydrous sodium sulfate. Then, the solvent was distilled off under reduced pressure, and a crude product thereby obtained was purified by silica gel column chromatography (eluting solution: methylene chloride/ethyl acetate=95/5) to obtain 0.96 g of the desired product (Compound No. 35 as described hereinafter) having a melting point of from 243° to 244° C.

Novel compounds are included in the compounds of the above formulas (II), (IV) and (V) useful as intermediates of the compounds of the present invention, and typical examples thereof will be given in the following Tables 1-1 to 1-3.

TABLE 1-1

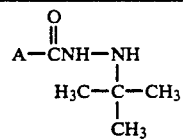

(II)

| Intermediate No. | A | Physical properties |
|---|---|---|
| 1 | benzo[b]furan-2-yl | m.p. 82–84° C. |
| 2 | quinolin-2-yl | Non-crystalline solid |
| 3 | quinolin-3-yl | m.p. 156–162° C. |
| 4 | 5-chlorobenzo[b]thiophen-3-yl | m.p. 143–145° C. |
| 5 | benzo[b]thiophen-2-yl | m.p. 147–148° C. |
| 6 | benzothiazol-2-yl | m.p. 115–119° C. |
| 7 | 6-methylbenzo[b]thiophen-2-yl | m.p. 167–169° C. |
| 8 | 4-chlorobenzo[b]thiophen-2-yl | m.p. 124–126° C. |
| 9 | 3-chlorobenzo[b]thiophen-2-yl | m.p. 145–146° C. |
| 10 | 5-nitrobenzo[b]thiophen-2-yl | m.p. 159–160° C. |
| 11 | thieno[2,3-b]thiophen-2-yl | m.p. 178–179° C. |
| 12 | 6-trifluoromethylbenzo[b]thiophen-2-yl | m.p. 160–161° C. |
| 13 | 5,6-dichlorobenzo[b]thiophen-2-yl | m.p. 195–197° C. |
| 14 | 6,7-dichlorobenzo[b]thiophen-2-yl | m.p. 187–189° C. |
| 15 | 5,6-dimethoxybenzo[b]thiophen-2-yl | Non-crystalline solid |
| 16 | 6-fluorobenzo[b]thiophen-2-yl | m.p. 175–176° C. |
| 17 | 5,6-difluorobenzo[b]thiophen-2-yl | m.p. 151–152° C. |
| 18 | thieno[3,2-b]thiophen-2-yl | m.p. 174–175° C. |
| 19 | 5-trifluoromethylbenzo[b]thiophen-2-yl | m.p. 155–156° C. |
| 20 | 7-trifluoromethylbenzo[b]thiophen-2-yl | m.p. 143–144° C. |
| 21 | 5-fluorobenzo[b]thiophen-2-yl | m.p. 153–155° C. |
| 22 | 4,5,6,7-tetrafluorobenzo[b]thiophen-2-yl | m.p. 181–183° C. |
| 23 | benzo[b]thiophen-6-yl | m.p. 152–154° C. |
| 24 | benzo[b]thiophen-5-yl | m.p. 137–138° C. |
| 25 | 5,7-difluorobenzo[b]furan-2-yl | — |
| 26 | 6-fluoroquinolin-2-yl | — |
| 27 | 6-fluorobenzothiazol-2-yl | — |
| 28 | 5,6-dihydro-4H-cyclopenta[b]thiophen-2-yl | m.p. 163–164° C. |
| 29 | 4,5,6,7-tetrahydrobenzo[b]thiophen-2-yl | m.p. 155–157° C. |
| 30 | thieno[3,4-b]thiophen-2-yl | m.p. 144–145° C. |
| 31 | 4-fluorobenzo[b]thiophen-2-yl | m.p. 148–149° C. |
| 32 | 2,3-dibromobenzo[b]thiophen-6-yl | m.p. 166–167° C. |
| 33 | 1,3-dihydrobenzo[c]thiophen-5-yl | m.p. 138–139° C. |
| 34 | 4,6-dihydrothieno[3,4-b]thiophen-2-yl | m.p. 182–183° C. |
| 35 | indan-2-yl | m.p. 75–76° C. |
| 36 | hexahydroindan-2-yl | Solid |

TABLE I-2

A-COY    (IV)

| Intermediate No. | A | Y | Physical properties |
|---|---|---|---|
| 37 | 6-trifluoromethylbenzo[b]thiophen-2-yl | Cl | Oil |
| 38 | 6-fluorobenzo[b]thiophen-2-yl | Cl | Oil |
| 39 | 5,6-difluorobenzo[b]thiophen-2-yl | Cl | Oil |

TABLE I-3

A-COOH    (V)

| Intermediate No. | A | Physical properties |
|---|---|---|
| 37 | 6-trifluoromethylbenzo[b]thiophen-2-yl | Solid |
| 38 | 6-fluorobenzo[b]thiophen-2-yl | Solid |

TABLE I-3-continued $$A\text{-COOH} \quad (V)$$

| Intermediate No. | A | Physical properties |
|---|---|---|
| 39 | 5,6-difluorobenzo[b]thiophen-2-yl | Solid |

Now, typical examples of the compounds of the formula (I) of the present invention wherein W is a hydrogen atom, will be presented in the following Table 2.

TABLE 2

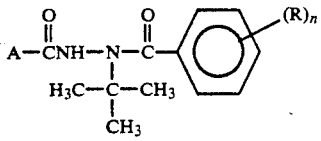

(I-1)

| Compound No. | A | (R)$_n$ | Physical properties |
|---|---|---|---|
| 1 | benzo[b]furan-2-yl | 3,5-(CH$_3$)$_2$ | m.p. 246–247° C. |
| 2 | quinolin-2-yl | 3,5-(CH$_3$)$_2$ | m.p. 169–171° C. |
| 3 | quinolin-3-yl | 3,5-(CH$_3$)$_2$ | m.p. 195–199° C. |
| 4 | 5-chlorobenzo[b]thiophen-3-yl | 3,5-(CH$_3$)$_2$ | m.p. 236–239° C. |
| 5 | benzo[b]thiophen-2-yl | 3,5-(CH$_3$)$_2$ | m.p. 211–213° C. |
| 6 | benzo[b]thiophen-2-yl | 2-Cl | m.p. 254–255° C. |
| 7 | benzo[b]thiophen-2-yl | 2-NO$_2$ | m.p. 221–222° C. |
| 8 | benzothiazol-2-yl | 3,5-(CH$_3$)$_2$ | m.p. 190–195° C. |
| 9 | benzothiazol-2-yl | 2-NO$_2$ | m.p. 182–187° C. |
| 10 | 6-methylbenzo[b]thiophen-2-yl | 3,5-(CH$_3$)$_2$ | m.p. 235–237° C. |
| 11 | 4-chlorobenzo[b]thiophen-2-yl | 3,5-(CH$_3$)$_2$ | m.p. 185–186° C. |
| 12 | 4-chlorobenzo[b]thiophen-2-yl | 3-CH$_3$ | m.p. 225–227° C. |
| 13 | 3-chlorobenzo[b]thiophen-2-yl | 3,5-(CH$_3$)$_2$ | m.p. 196–197° C. |
| 14 | 3-chlorobenzo[b]thiophen-2-yl | 2-NO$_2$ | Non-crystalline solid |
| 15 | 5-nitrobenzo[b]thiophen-2-yl | 3,5-(CH$_3$)$_2$ | m.p. 229–230° C. |
| 16 | 5-nitrobenzo[b]thiophen-2-yl | 2-NO$_2$ | m.p. 266–267° C. |
| 17 | thieno[2,3-b]thiophen-2-yl | 3,5-(CH$_3$)$_2$ | m.p. 243–245° C. |
| 18 | 6-trifluoromethylbenzo[b]thiophen-2-yl | 3,5-(CH$_3$)$_2$ | m.p. 195–198° C. |
| 19 | 5,6-dichlorobenzo[b]thiophen-2-yl | 3,5-(CH$_3$)$_2$ | m.p. 235–238° C. |
| 20 | 6,7-dichlorobenzo[b]thiophen-2-yl | 3,5-(CH$_3$)$_2$ | m.p. 238–240° C. |
| 21 | 5,6-dimethoxybenzo[b]thiophen-2-yl | 3,5-(CH$_3$)$_2$ | m.p. 170–173° C. |
| 22 | 6-fluorobenzo[b]thiophen-2-yl | 3,5-(CH$_3$)$_2$ | m.p. 243–244° C. |
| 23 | 5,6-difluorobenzo[b]thiophen-2-yl | 3,5-(CH$_3$)$_2$ | m.p. 242–244° C. |
| 24 | thieno[3,2-b]thiophen-2-yl | 3,5-(CH$_3$)$_2$ | m.p. 225–227° C. |
| 25 | 5-trifluoromethylbenzo[b]thiophen-2-yl | 3,5-(CH$_3$)$_2$ | m.p. 191–196° C. |
| 26 | 7-trifluoromethylbenzo[b]thiophen-2-yl | 3,5-(CH$_3$)$_2$ | m.p. 197–199° C. |
| 27 | 5-fluorobenzo[b]thiophen-2-yl | 3,5-(CH$_3$)$_2$ | m.p. 224–226° C. |
| 28 | 4,5,6,7-tetrafluorobenzo[b]thiophen-2-yl | 3,5-(CH$_3$)$_2$ | m.p. 249–250° C. |
| 29 | benzo[b]thiophen-6-yl | 3,5-(CH$_3$)$_2$ | m.p. 203–204° C. |
| 30 | benzo[b]thiophen-5-yl | 3,5-(CH$_3$)$_2$ | m.p. 226–227° C. |
| 31 | 5,7-difluorobenzo[b]furan-2-yl | 3,5-(CH$_3$)$_2$ | — |
| 32 | 6-fluoroquinolin-2-yl | 3,5-(CH$_3$)$_2$ | — |
| 33 | 6-fluorobenzothiazol-2-yl | 3,5-(CH$_3$)$_2$ | — |
| 34 | 5,6-dihydro-4H-cyclopenta[b]thiophen-2-yl | 3,5-(CH$_3$)$_2$ | m.p. 231–232° C. |
| 35 | 4,5,6,7-tetrahydrobenzo[b]thiophen-2-yl | 3,5-(CH$_3$)$_2$ | m.p. 243–244° C. |
| 36 | thieno[3,4-b]thiophen-2-yl | 3,5-(CH$_3$)$_2$ | m.p. 248–250° C. |
| 37 | 4-fluorobenzo[b]thiophen-2-yl | 3,5-(CH$_3$)$_2$ | m.p. 214–215° C. |
| 38 | 2,3-dibromobenzo[b]thiophen-6-yl | 3,5-(CH$_3$)$_2$ | m.p. 153–155° C. |
| 39 | 1,3-dihydrobenzo[c]thiophen-5-yl | 3,5-(CH$_3$)$_2$ | m.p. 123–125° C. |
| 40 | 4,6-dihydrothieno[3,4-b]thiophen-2-yl | 3,5-(CH$_3$)$_2$ | m.p. 252–253° C. |
| 41 | 5,6-dihydro-4H-cyclopenta[b]thiophen-2-yl | 2-Cl | m.p. 236–237° C. |
| 42 | 4,5,6,7-tetrahydrobenzo[b]thiophen-2-yl | 2-Cl | m.p. 274–276° C. |
| 43 | 4,5,6,7-tetrahydrobenzo[b]thiophen-2-yl | 3-CH$_3$ | m.p. 256–257° C. |
| 44 | 5,6-dihydro-4H-cyclopenta[b]thiophen-2-yl | 3-CH$_3$ | m.p. 203–204° C. |
| 45 | 5,6-dihydro-4H-cyclopenta[b]thiophen-2-yl | 4-F-3-CH$_3$ | m.p. 203–204° C. |
| 46 | 4,5,6,7-tetrahydrobenzo[b]thiophen-2-yl | 4-F-3-CH$_3$ | m.p. 200–201° C. |
| 47 | 5,6-dihydro-4H-cyclopenta[b]thiophen-2-yl | 2-F-5-CH$_3$ | m.p. 215–216° C. |
| 48 | 4,5,6,7-tetrahydrobenzo[b]thiophen-2-yl | 2-F-5-CH$_3$ | m.p. 256–257° C. |
| 49 | 5,6-dihydro-4H-cyclopenta[b]thiophen-2-yl | 2-Cl-5-CH$_3$ | m.p. 205–206° C. |
| 50 | 5,6-dihydro-4H-cyclopenta[b]thiophen-2-yl | 4-Cl-3-CH$_3$ | m.p. 238–239° C. |
| 51 | 4,5,6,7-tetrahydrobenzo[b]thiophen-2-yl | 2-Cl-5-CH$_3$ | m.p. 221–222° C. |
| 52 | 5,6-dihydro-4H-cyclopenta[b]thiophen-2-yl | 2-Cl-3-CH$_3$ | m.p. 197° C. |
| 53 | 4,5,6,7-tetrahydrobenzo[b]thiophen-2-yl | 2-Cl-3-CH$_3$ | m.p. 204–205° C. |
| 54 | 5,6-dihydro-4H-cyclopenta[b]thiophen-2-yl | 2-F-3-CH$_3$ | m.p. 167–168° C. |
| 55 | 4,5,6,7-tetrahydrobenzo[b]thiophen-2-yl | 2-F-3-CH$_3$ | m.p. 232–233° C. |
| 56 | 5,6-dihydro-4H-cyclopenta[b]thiophen-2-yl | 3-OCH$_3$ | m.p. 176–177° C. |
| 57 | 5,6-dihydro-4H-cyclopenta[b]thiophen-2-yl | 4-F-3,5-(CH$_3$)$_2$ | m.p. 252–253° C. |
| 58 | 5,6-dihydro-4H-cyclopenta[b]thiophen-2-yl | 3,5-F$_2$ | m.p. 257° C. |
| 59 | indane-2-yl | 3,5-(CH$_3$)$_2$ | m.p. 232.4° C. |

TABLE 2-continued

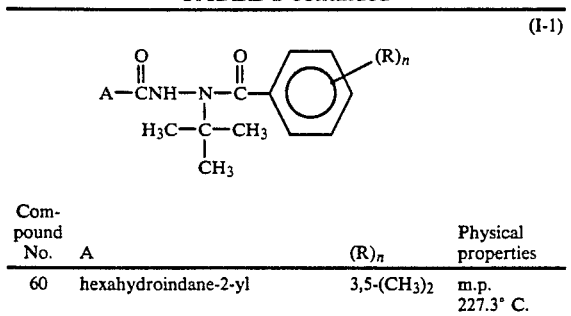

| Compound No. | A | (R)$_n$ | Physical properties |
|---|---|---|---|
| 60 | hexahydroindane-2-yl | 3,5-(CH$_3$)$_2$ | m.p. 227.3° C. |

Among the compounds of the formula (I), those represented by the following formula (I-2) also exhibit high pesticidal activities:

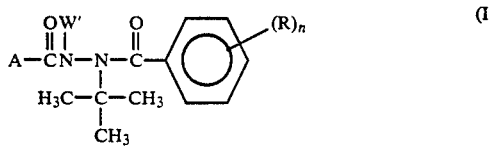

wherein A, R and n are as defined above, and W' is a cyano group, —COCOOR', —S—N(R")COOR' or —CH$_2$OCOR', wherein R' and R" are as defined above.

The compounds of the formula (I-2) can be prepared, for example, by the following process or in accordance with the methods disclosed in e.g. EP 0395581A, EP 0398842A, U.S. Pat. No. 4,857,550 and Japanese Unexamined Patent Publication No. 207066/1990.

(I-1)+W'-G→(I-2)

In the above formula, W' is as defined above, and G is a chlorine atom or a bromine atom.

The above reaction is conducted usually in the presence of a solvent and a base at a reaction temperature of from −100° C. to +150° C., preferably from −80° C. to +100° C. for a reaction time of from 0.1 to 24 hours, preferably from 0.2 to 3 hours. As the solvent, a solvent inert to the reaction, such as an aromatic hydrocarbon such as benzene or toluene; an ether such as diethyl ether or tetrahydrofuran; or an aprotic polar solvent such as acetonitrile, dimethylformamide, dimethylsulfoxide or hexamethylphosphoric acid triamide, may be used. These solvents may be used alone or in combination as a mixture.

The base may suitably be selected from inorganic bases such as sodium hydride and potassium hydride; organic lithium compounds such as n-butyl lithium, tert-butyl lithium and phenyl lithium; and organic bases such as triethylamine and pyridine.

Now, specific Synthesis Examples of the compounds of the present invention wherein W is W' wherein W' is as defined above, will be described.

SYNTHESIS EXAMPLE 5

Synthesis of N'-t-butyl-N-cyano-N'-3,5-dimethylbenzoyl-N-5,6-dihydro-4H-cyclopenta[b]thiophene-2-carbohydrazide (Compound No. 61)

80 mg of a 60% sodium hydride dispersion in a mineral oil, was gradually added to a solution having 500 mg of N'-t-butyl-N'-3,5-dimethylbenzoyl-N-5,6-dihydro-4H-cyclopenta[b]thiophene-2-carbohydrazide (above Compound No. 34) dissolved in a solvent mixture comprising 5 ml of tetrahydrofuran and 1 ml of hexamethylphosphoric acid triamide. After the addition, the reaction solution was stirred at room temperature for 15 minutes, and then 240 mg of cyanogen bromide was added thereto. The mixture was reacted for one hour under reflux.

After completion of the reaction, the reaction solution was cooled to room temperature. The reaction product was put into water and extracted with ethyl acetate. Then, the organic layer was washed with water and dried over anhydrous sodium sulfate. Then, the solvent was distilled off under reduced pressure, and a crude product thereby obtained was purified by silica gel column chromatography (eluting solution: n-hexane/ethyl acetate=9/1) to obtain 310 mg of the desired product (Compound No. 61) having a refractive index of 1.5631 (20.6° C.).

In the same manner as in the above Synthesis Example, the following compounds were prepared. Compound No. 62: N'-t-butyl-N'-3,5-dimethylbenzoyl-N-ethoxalyl-N-5,6-dihydro-4H-cyclopenta[b]thiophene-2-carbohydrazide (refractive index: 1.5412 at 46.4° C.)
Compound No. 63: N'-t-butyl-N'-3,5-dimethylbenzoyl-N-[(N"-methyl-N"-n-butoxycarbonyl)aminosulphenyl]-N-5,6-dihydro-4H-cyclopenta[b]thiophene-2-carbohydrazide (viscous oil)

The compounds of the formula (I) of the present invention exhibit excellent pesticidal activities as active ingredients for pesticides. For instance, they are effective against plant parasitic mites such as two-spotted spider mite (*Tetranychus urticae*), carmine spider mite (*Tetranychus cinnabarinus*) or citrus red mite (*Panonychus citri*) or bulb mite (*Rhizoglyphus echinopus*); agricultural insect pests such as diamondback moth (*Plutella xylostella*), cabbage armyworm (*Mamestra brassicae*), common cutworm (*Spodoptera litura*), rice leafroller (*Cnaphalocrocis medinalis*), Adoxophyes sp., colorado potato beetle (*Leptinotarsa decemlineata*), codling moth (*Laspeyresia pomonella*), bollworm (*Heliothis zea*), tobacco budworm (*Heliothis virescens*), boll weevil (*Anthonomus grandis*), gypsy moth (*Lymantria dispar*), cucurbit leaf beetle (*Aulacophora femoralis*), aphids, planthoppers, leafhoppers, scales, bugs, whiteflies, thrips, grasshoppers, anthomyiid flies, scarabs, black cutworm (*Agrotis ipsilon*), cutworm (*Agrotis segetum*) or ants; hygienic insect pests such as tropical rat mite (*Ornithonyssus bacoti*), cockroaches, housefly (*Musca domestica*) or house mosquito (*Culex pipiens pallens*); stored grain insect pests such as angoumois grain moth (*Sitotroga cerealella*), azuki bean weevil (*Callosobruchus chinensis*), confused flour beetle (*Tribolium confusum*) or mealworms; household goods insect pests such as casemaking clothes moth (*Tinea pellionella*), black carpet beetle (*Anthrenus scrophularidae*) or subterranean termites; and other parasites on domestic animals such as fleas, lice or flies. Furthermore, they are also effective against the soil pests. The soil pests in the present invention are gastropods such as slugs or snails, or isopods such as pillbugs or sowbugs. The compounds of the present invention exhibit particularly excellent pesticidal activities against Lepidoptera pests among the above mentioned various pests. Further, they are effective also against insect pests such as diamondback moth and housefly having the resistance to organophosphorus and pyrethroid insecticides. Furthermore, the compounds of the present invention have systemic properties. Therefore, by their application to soil treatment, it is possible to control not only noxious insects, mites, nematodes, gastropods and isopods in soil but also foliage pests. The compounds of the present invention are highly safe to mammals, fishes and useful insects and thus suitable for use as pesticides.

To use as active ingredients for pesticides, the compounds of the present invention may be formulated together with agricultural adjuvants into various forms such as dusts, granules, wettable powders, water dispersible granules, suspension concentrates, emulsifiable concentrates, aerosols or pastes, just like conventional agricultural chemicals.

Such formulations are usually composed of 0.1–90 parts by weight, preferably 0.5–90 parts by weight, more preferably 0.5–80 parts by weight, of active ingredient and 10–99.9 parts by weight, preferably 10–99.5 parts by weight, more preferably 20–99.5 parts by weight, of agricultural adjuvants. When such formulations are to be actually used, they may be used as they are or after being diluted with suitable diluents such as water to a predetermined concentration.

As the agricultural adjuvants, there may be mentioned carriers, emulsifiers, suspending agents, dispersants, extenders, penetrating agents, wetting agents, thickeners, defoaming agents, stabilizers and anti-freezing agents. They may be added as the case requires. The carriers may be divided into solid carriers and liquid carriers. As the solid carriers, there may be mentioned powders of animal and plant origin, such as starch, activated carbon, soybean flour, wheat flour, wood powder, fish powder or powdered milk; mineral powders such as talc, kaolin, bentonite, calcium carbonate, zeolite, diatomaceous earth, white carbon, clay or alumina; sulfur powder; or anhydrous sodium salfate. As the liquid carriers, there may be mentioned water; alcohols such as methyl alcohol or ethylene glycol; ketones such as acetone, methyl ethyl ketone or N-methyl-2-pyrrolidone; ethers such as dioxane or tetrahydrofuran; aliphatic hydrocarbons such as kerosene; aromatic hydrocarbons such as xylene, trimethylbenzene, tetramethylbenzene, cyclohexane or solvent naphtha; halogenated hydrocarbons such as chloroform or chlorobenzene; acid amides such as dimethylformamide; esters such as ethyl acetate or glycerine ester of a fatty acid; nitriles such as acetonitrile; sulfur-containing compounds such as dimethyl sulfoxide; or vegetable oils such as soybean oil or corn oil.

Now, Formulation Examples of pesticides containing the compounds of the present invention as active ingredients, will be described. However, the compounds as active ingredients, the types of agricultural adjuvants, the blend ratios or the types of the formulations are not restricted to these specific Examples.

| FORMULATION EXAMPLE 1 | |
|---|---|
| (1) Compound No. 5 | 20 parts by weight |
| (2) Kaoline | 52 parts by weight |
| (3) Sodium lignin sulfonate | 8 parts by weight |
| (4) White carbon | 20 parts by weight |

The above components are uniformly mixed to obtain a wettable powder.

| FORMULATION EXAMPLE 2 | |
|---|---|
| (1) Compound No. 34 | 5 parts by weight |
| (2) Talc | 95 parts by weight |

The above components are uniformly mixed to obtain a dust.

| FORMULATION EXAMPLE 3 | |
|---|---|
| (1) Compound No. 35 | 20 parts by weight |
| (2) N-methyl-2-pyrrolidone | 10 parts by weight |
| (3) Polyoxyethylenealkylphenyl ether | 10 parts by weight |
| (4) Xylene | 60 parts by weight |

The above components are uniformly mixed and dissolved to obtain an emulsifiable concentrate.

| FORMULATION EXAMPLE 4 | |
|---|---|
| (1) Kaoline | 83 parts by weight |
| (2) Sodium lignin sulfonate | 2 parts by weight |
| (3) Polyoxyethylenealkylaryl sulfate | 5 parts by weight |
| (4) Fine silica powder | 10 parts by weight |

A mixture of the above components is mixed with comound No. 17 in weight ratio of 4:1 to obtain a wettable powder.

| FORMULATION EXAMPLE 5 | |
|---|---|
| (1) Compound No. 34 | 40 parts by weight |
| (2) Oxylated polyalkylphenol phosphate-triethanolamine | 2 parts by weight |
| (3) Silicone | 0.2 part by weight |
| (4) Xanthane gum | 0.1 part by weight |
| (5) Ethylene glycol | 5 parts by weight |
| (6) Water | 52.7 parts by weight |

The above components are uniformly mixed and pulverized to obtain an water based suspension concentrate.

| FORMULATION EXAMPLE 6 | |
|---|---|
| (1) Compound No. 5 | 75 parts by weight |
| (2) Sodium polycarboxylate | 13.5 parts by weight |
| (3) Anhydrous sodium sulfate | 10 parts by weight |
| (4) Dextrine | 0.5 part by weight |
| (5) Sodium alkylsulfonate | 1 part by weight |

The above components are introduced in a high speed mixing pulverizer, and 20% of water is added thereto, and the mixture are granulated and dried to obtain a water dispersible granule.

| FORMULATION EXAMPLE 7 | |
|---|---|
| (1) Compound No. 22 | 5 parts by weight |
| (2) Bentonite | 33 parts by weight |
| (3) Kaoline | 57 parts by weight |
| (4) Sodium lignin sulfonate | 5 parts by weight |

To the above components, a suitable amount of water for granulation is added, and the mixture is mixed and granulated to obtain a granule.

| FORMULATION EXAMPLE 8 | |
|---|---|
| (1) Compound No. 24 | 2.5 parts by weight |

-continued
| FORMULATION EXAMPLE 8 | |
|---|---|
| (2) N-methyl-2-pyrrolidone | 2.5 parts by weight |
| (3) Soybean oil | 95.0 parts by weight |

The above components are uniformly mixed and dissolved to obtain an ultra low volume formulation.

| FORMULATION EXAMPLE 9 | |
|---|---|
| (1) Compound No. 30 | 5 parts by weight |
| (2) N-methyl-2-pyrrolidone | 5 parts by weight |
| (3) Polyoxyethylenealkylaryl ether | 10 parts by weight |
| (4) Xylene | 80 parts by weight |

The above components are uniformly mixed to obtain an emulsifiable concentrate.

| FORMULATION EXAMPLE 10 | |
|---|---|
| (1) Compound NO. 43 | 10 parts by weight |
| (2) Corn oil | 77 parts by weight |
| (3) Polyoxyethylene hardened castor oil | 12 parts by weight |
| (4) Organic bentonite | 1 part by weight |

The above components are uniformly mixed and pulverized to obtain an oil based suspension concentrate.

Further, the pesticides containing the compounds of the present invention as active ingredients may be used in admixture with or in combination with other agricultural chemicals such as insecticides, miticides, nematicides, fungicides, antiviral agents, attractants, herbicides or plant growth regulators, as the case requires. In some cases, the effectiveness will be improved by such combination.

For instance, as such insecticides, miticides or nematicides, there may be mentioned organophosphorus compounds such as O-(4-bromo-2-chlorophenyl) O-ethyl S-propyl phosphorothioate, O-(2,2-dichlorovinyl) O,O-dimethyl phosphate, O-ethyl O-[3-methyl-4-(methylthio)phenyl] N-isopropylphosphoramidate, O,O-dimethyl O-(4-nitro-m-tolyl) phosphorothioate, O-ethyl O-(4-nitrophenyl) phenylphosphonothioate, O,O-diethyl O-(2-isopropyl-6-methylpyrimidin-4-yl) phosphorothioate, O,O-dimethyl O-(3,5,6-trichloro-2-pyridyl) phosphorothioate, O,S-dimethyl N-acetylphosphoramidothioate, O-(2,4-dichlorophenyl) O-ethyl S-propyl phosphorodithioate or (RS)-S-sec-butyl O-ethyl 2-oxo-1,3-thiazolydin-3-yl phosphonothioate; carbamate compounds such as 1-naphthyl N-methylcarbamate, 2-isopropoxyphenyl N-methylcarbamate, 2-methyl-2-(methylthio)propionaldehyde O-methylcarbamoyloxime, 2,3-dihydro-2,2-dimethylbenzofuran-7-yl N-methylcarbamate, dimethyl N,N'-[thiobis{(methylimino)carbonyloxy}] bisethanimidothioate, S-methyl N-(methylcarbamoyloxy) thioacetoimidate, N,N-dimethyl-2-methylcarbamoyloxyimino-2-(methylthio)acetamide, 2-(ethylthiomethyl)phenyl N-methylcarbamate, 2-dimethylamino-5,6-dimethylpyrimidin-4-yl N,N-dimethylcarbamate or 2-sec-butylphenyl N-methylcarbamate; nereistoxin derivatives such as S,S'-2-dimethyl aminotrimethylene bis(thiocarbamate) or N,N-dimethyl-1,2,3-trithian-5-yl amine; organic chlorine compounds such as 2,2,2-trichloro-1,1-bis(4-chlorophenyl)ethanol or 4-chlorophenyl-2,4,5-trichlorophenyl sulfone; organic metal compounds such as bis[tris(2-methyl-2-phenylpropyl)tin]oxide; pyrethroid compounds such as (RS)-α-cyano-3-phenoxybenzyl (RS)-2-(4-chlorophenyl)-3-methylbutyrate, 3-phenoxybenzyl (1RS)-cis,trans-3-(2,2-dichlorovinyl)-2,2-dimethylcyclopropanecarboxylate, (RS)-α-cyano-3-phenoxybenzyl (1RS)-cis,trans-3-(2,2-dichlorovinyl)-2,2-dimethylcyclopropanecarboxylate, (S)-α-cyano-3-phenoxybenzyl (1R)-cis-3-(2,2-dibromovinyl)-2,2-dimethylcyclopropanecarboxylate, (RS)-α-cyano-3-phenoxybenzyl (1RS)-cis,trans-3-(2-chloro-3,3,3-trifluoropropenyl)-2,2-dimethylcyclopropanecarboxylate, 4-methyl-2,3,5,6-tetrafluorobenzyl-3-(2-chloro-3,3,3-trifluoro-1-propenyl)-2,2-dimethylcyclopropane carboxylate or 2-(4-ethoxyphenyl)-2-methylpropyl 3-phenoxybenzyl ether (common name: ethofenprox; hereinafter referred to simply as Compound No. A-1); benzoyl urea compounds such as 1-(4-chlorophenyl)-3-(2,6-difluorobenzoyl)urea, 1-[3,5-dichloro-4-(3-chloro-5-trifluoromethyl-2-pyridyloxy)-phenyl]-3-(2,6-difluorobenzoyl)urea or 1-(3,5-dichloro-2,4-difluorophenyl)-3-(2,6-difluorobenzoyl)urea; juvenile hormone analogs such as isopropyl (2E,4E)-11-methoxy-3,7,11-trimethyl-2,4-dodecadienoate; pyridazinone compounds such as 2-tert-butyl-5-(4-tert-butylbenzylthio)-4-chloro-3(2H)-pyridazinone; pyrazole compounds such as tert-butyl 4-[(1,3-dimethyl-5-phenoxypyrazol-4-yl)methylene aminooxymethyl] benzoate; nitro compounds such as 1-(6-chloro-3-pyridylmethyl)-N-nitro-imidazolidin-2-ylideneamine (common name: imidacloprid; hereinafter referred to simply as Compound No. A-2), 1-[N-(6-chloro-3-pyridylmethyl)-N-ethylamino]-1-methylamino-2-nitroethylene (EP 302389A; hereinafter referred to simply as Compound No. A-3), 2-methylamino-2-[N-methyl-N-(6-chloro-3-pyridylmethyl)amino]-1-nitroethylene (EP 302389A; hereinafter referred to simply as Compound No. A-4), 1-(6-chloro-3-pyridylmethyl)amino-1-dimethylamino-2-nitroethylene (EP 302389A; hereinafter referred to simply as Compound No. A-5), 1-(6-chloro-3-pyridylmethyl)-2-(1-nitro-2-allylthioethylidene)imidazolidine (EP 437784A; hereinafter referred to simply as Compound No. A-6), 1-(6-chloro-3-pyridylmethyl)-2-(1-nitro-2-ethylthioethylidene)imidazolidine (EP 437784A; hereinafter referred to simply as Compound No. A-7), 1-(6-chloro-3-pyridylmethyl)-2-(1-nitro-2-β-methylallylthioethylidene)imidazolidine (EP 437784A; hereinafter referred to simply as Compound No. A-8), 1-(6-chloro-3-pyridylmethyl)-3-methyl-2-nitroguanidine (EP 383091A; hereinafter referred to simply as Compound No. A-9), 1-(6-chloro-3-pyridylmethyl)-3,3-dimethyl-2-nitroguanidine (EP 383091A; hereinafter referred to simply as Compound No. A-10), 3-(6-chloro-3-pyridylmethyl)-2-nitromethylene-thiazolidine (EP 192060A; hereinafter referred to simply as Compound No. A-11), 1-(6-chloro-3-pyridylmethyl)-2-(nitromethylene)imidazolidine (EP 163855A: hereinafter referred to simply as Compound No. A-12), 6-(6-chloro-3-pyridylmethylamino)-1,3-dimethyl-5-nintro-1,2,3,4-tetrahydropyrimidine (EP 366085A; hereinafter referred to simply as Compound No. A-13) or 1-(6-chloro-3-pyridylmethyl)-5-nitro-3-methyl-6-methylamino-1,2,3,4-tetrahydropyrimidine (EP 366085A; hereinafter referred to simply as Compound No. A-14); dinitro compounds; organic sulfur compounds; urea compounds; triazine compounds; hydrazine compounds; and other compounds such as 2-tert-butylimino-3-isopropyl-5-phenyl-3,4,5,6-tetrahydro-2H-1,3,5-thiadiazin-4-one (common name: buprofezin; hereinafter referred to simply as Compound No. A-15), trans-(4-chlorophenyl)-N-cyclohexyl-4-methyl-2-oxothiazolidinon-3-carboxamide, N-methylbis(2,4-xylyliminomethyl)amine, N'-(4-chloro-o-tolyl)-N,N-dimethylformamidine or (4-ethoxyphenyl)-[3-(4-fluoro-3-phenoxyphenyl)-propyl](dimethyl)silane (common name: silafluofen; hereinafter referred to simply as Compound No. A-16). Further, microbial insecticides such as *Bacillus thurigiensis* agent or nuclear polyhedrosis virus; antibiotics such as avermectin or milbemycin; or the like may also be used in admixture with or in combination with the pesticides of the present invention. Among these insecticides, miticides and nematicides, Compound Nos. A-1, A-2, A-3, A-4, A-5, A-6, A-7, A-8, A-9, A-10, A-11, A-12, A-13, A-14, A-15 and A-16 are preferred. More preferred are Compound Nos. A-1, A-2, A-3, A-6, A-15 and A-16. It is particularly preferred that at least one of Compound Nos. 5, 34 and 35 of the present invention and at least one of Compound Nos. A-1, A-2, A-3, A-6, A-15 and A-16 are mixed, and the mixture is applied so that the former would be from 50 to 5,000 g/ha and the later would be from 10 to 5,000 g/ha, whereby excellent pesticidal effects will be obtained against insect pests such as rice leafroller (*Cnaphalocrocis medinalis*), Adoxophyes sp., planthoppers and leafhoppers.

As the fungicides, there may be mentioned organophosphorus compounds such as S-benzyl O,O-diisopropyl phosphorothioate, O-ethyl S,S-diphenyl phosphorodithioate or aluminium ethyl hydrogen phosphonate; organic chlorine compounds such as 4,5,6,7-tetrachlorophthalide or tetrachloroisophthalonitrile; dithiocarbamate compounds such as polymeric manganese ethylenebis(dithiocarbamate), polymeric zinc ethylenebis(dithiocarbamate), manganese ethylenebis(dithiocarbamate) complex with zinc salt, dizinc bis(dimethyldithiocarbamate)ethylenebis(dithiocarbamate) or polymeric zinc propylenebis(dithiocarbamate); N-halogenothioalkyl compounds such as 3a,4,7,7a-tetrahydro-N-(trichloromethylsulfenyl)phthalimide, 3a,4,7,7a-tetrahydro-N-(1,1,2,2-tetrachloroethylsulfenyl)phthalimide or N-(trichloromethylsulfenyl)phthalimide; dicarboxy imide compounds such as 3-(3,5-dichlorophenyl)-N-isopropyl-2,4-dioxoimidazolidine-1-carboxamide, (RS)-3-(3,5-dichlorophenyl)-5-methyl-5-vinyl-1,3-oxazolidine-2,4-dione or N-(3,5-dichlorophenyl)-1,2-dimethylcyclopropane-1,2-dicarboximide; benzimidazole compounds such as methyl 1-(butylcarbamoyl)-benzimidazol-2-yl-carbamate or dimethyl 4,4'-(o-phenylene)bis(3-thioallophanate); azole compounds such as 1-(4-chlorophenoxy)-3,3-dimethyl-1-(1H-1,2,4-triazol-1-yl)butanone, 1-(biphenyl-4-yloxy)-3,3-dimethyl-1-(1H-1,2,4-triazol-1-yl)butan-2-ol, 1-[N-(4-chloro-2-trifluoromethylphenyl)-2-propoxyacetoimidoyl]imidazole, 1-[2-(2,4-dichlorophenyl)-4-ethyl-1,3-dioxolan-2-ylmethyl]-1H-1,2,4-triazole, 1-[2-(2,4-dichlorophenyl)-4-propyl-1,3-dioxolan-2-ylmethyl]-1H-1,2,4-triazole or 1-[2-(2,4-dichlorophenyl)pentyl]-1H-1,2,4-triazole; carbinol compounds such as 2,4'-dichloro-α-(pyrimidin-5-yl)benzhydryl alcohol or (±)-2,4'-difluoro-α-(1H-1,2,4-triazol-1-ylmethyl)benzhydryl alcohol; benzanilide compounds such as 3'-isopropoxy-o-toluanilide or α,α,α-trifluoro-3'-isopropoxy-o-toluanilide; phenylamide compounds such as methyl N-(2-methoxyacetyl)-N-(2,6-xylyl)-DL-alaninate; pyridinamine compounds such as 3-chloro-N-(3-chloro-2,6-dinitro-4-α,α,α-trifluorotolyl)-5-trifluoromethyl-2-pyridinamine; piperazine compounds; morpholine compounds; anthraquinone compounds; quinoxaline compounds; crotonic acid compounds; sulfenic acid compounds; urea compounds and other compounds such as diisopropyl 1,3-dithiolan-2-ylidenemalonate, 5-methyl-1,2,4-triazolo[3,4-b]benzothiazole, 1,2,5,6-tetrahydropyrrolo[3,2,1-ij]quinolin-4-one, 6-(3,5-dichloro-4-methylphenyl)-3(2H)-pyridazinone, 3-allyloxy-1,2-benzisothiazole-1,1-dioxide or 1-(4-chlorobenzyl)-1-cyclopentyl-3-phenylurea. Further, antibiotic substances such as validamycin A may also be used in admixture with or in combination with the pesticides of the present invention.

The blend ratio of the compound of the present invention to other agricultural chemical is usually within a range of from 1:100 to 100:1, preferably from 1:50 to 50:1. The pesticide containing the compound of the present invention as active ingredient is applied in an active ingredient concentration of from 1 to 20,000 ppm, preferably from 1 to 2,000 ppm, more preferably from 10 to 1,000 ppm. The active ingredient concentration may optionally be changed depending upon the formulation, the manner, purpose, timing or place of the application and the abundance of the insect pests. For instance, aquatic noxious insects can be controlled by applying the formulation having the above-mentioned concentration to the site of the outbreak, and thus, the concentration of the active ingredient in water is less than the above-mentioned range.

The amount of the application of the active ingredient per unit surface area is usually from about 1 to 50,000 g, preferably from 10 to 10,000 g, more preferably from 50 to 5,000 g, per hectare. However, in a certain special case, the amount of the application may be outside the above range.

Various formulations containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a feed containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

TEST EXAMPLE 1

Insecticidal Test Against Common Cutworm (*Spodoptera litura*)

Each formulation containing an active ingredient was dispersed in water to obtain a dispersion containing the active ingredient at a concentration of 800 ppm. Leaves of cabbage were dipped in the dispersion for about 10 seconds and then dried in air. A sheet of moistened filter paper was placed in a Petri dish having a diameter of 9 cm, and the dried leaves of cabbage were put on the filter paper. Ten larvae of common cutworm (*Spodoptera litura*) in second or third instar were released on the leaves, and the Petri dish was covered and kept in a constant temperature chamber with lightening at a temperature of 26° C. On the 5th day after release, dead insects were counted, and the mortality was calculated in accordance with the following equation.

$$\text{Mortality (\%)} = \frac{\text{Number of dead insects}}{\text{Number of insects released}} \times 100$$

As the result, the mortality was 100% with each of Compounds Nos. 1, 3, 5, 7–11, 13, 14, 17–20, 22–24, 27, 29, 30, 34, 35, 36, 37, 39–52 and 54–63, and the mortality was 90% with each of Compounds Nos. 2 and 6.

TEST EXAMPLE 2

Insecticidal Test Against Diamondback (*Plutella xylostella*)

The test was conducted in the same manner as in Test Example 1 except that the common cutworm in second or third instar was changed to diamonback (*Plutella xylestella*) in second or third instar, and the mortality was calculated in the same manner. The mortality was 100% with each of Compounds Nos. 1, 5, 7, 8, 10, 11, 14, 17, 19, 20, 22, 24, 27, 29, 30, 34, 35, 37, 39, 41, 43, 44, 47, 50, 57, 61, 62 and 63.

TEST EXAMPLE 3

Insecticidal Test Against Rice Leafroller (*Cnaphalocrocis medinalis*)

Each formulation containing an active ingredient was dispersed in water to obtain a dispersion containing the active ingredient at a concentration of 50 ppm. Leaves of corn were dipped in the dispersion for about 10 seconds and then dried in air. A sheet of moistened filter paper was placed in an ice cream cup having a diameter of 8 cm, and the dried leaves were put on the filter paper. Five larvae of rice leafroller (*Cnaphalocrocis medinalis*) in second or third instar were released on the leaves, and the ice cream cup was covered and kept in a constant temperature chamber with lightening at a temperature of 26° C. On the 5th day after release, dead insects were counted, and the mortality was calculated in the same manner as in Test Example 1.

The mortality was 100% with each of Compounds Nos. 5, 17, 22, and 34.

TEST EXAMPLE 4

Insecticidal Test Against *Adoxophyes* sp.

Each formulation containing an active ingredient was dispersed in water to obtain a dispersion containing the active ingredient at a concentration of 50 ppm. A small piece of an artificial feed (tradename: Insecta LF ®, manufactured by Nippon Nosan Kogyo K.K.) was dipped in the dispersion for about 60 seconds and then left to stand at room temperature for about one hour. A sheet of filter paper was placed in an.ice cream cup having a diameter of 8 cm, and the treated artificial feed was put on the filter paper. Ten larvae of Adoxophyes sp. in second or third instar were released thereon, and the ice cream cup was covered and kept in a constant temperature chamber with lightening at a temperature of 26° C. On the 8th or 9th day after release, dead insects were counted, and the mortality was calculated in the same manner as in Test Example 1.

The mortality was 100% with each of Compounds Nos. 5,34 and 35.

What is claimed is:

1. A hydrazine compound of the formula (I) or its salt:

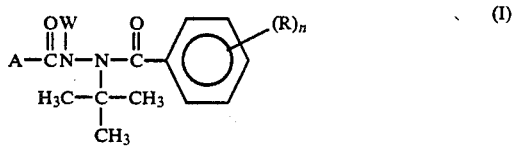

wherein A is a benzothienyl group which may be substituted, a thienothienyl group which may be substituted, a dihydrocyclopentathienyl group which may substituted, a tetrahydrobenzothienyl group which may be substituted, W is a hydrogen atom, R is a halogen atom or an alkyl group which may be substituted by a halogen atom, n is 1 or 2, provided that when n is 2, the plurality of R may be the same or different.

2. The compound according to claim 1, wherein A is a benzothienyl group which may be substituted, a dihydrocyclopentathienyl group which may be substituted, or a tetrahydrobenzothienyl group which may be substituted.

3. The compound according to claim 1, wherein A is a dihydrocyclopentathienyl group which may be substituted, or a tetrahydrobenzothienyl group which may be substituted.

4. The compound according to claim 1, which is N'-t-butyl-N'-3,5-dimethylbenzoyl-N-benzo[b]thiophene-2-carbohydrazide.

5. The compound according to claim 1, which is N'-t-butyl-N'-3,5-dimethylbenzoyl-N-5,6-dihydro-4H-cyclopenta[b]thiophene-2-carbohydrazide.

6. The compound according to claim 1, which is N'-t-butyl-N'-3,5-dimethylbenzoyl-N-4,5,6,7-tetrahydrobenzo[b]thiophene-2-carbohydrazide.

* * * * *